Figure 1:
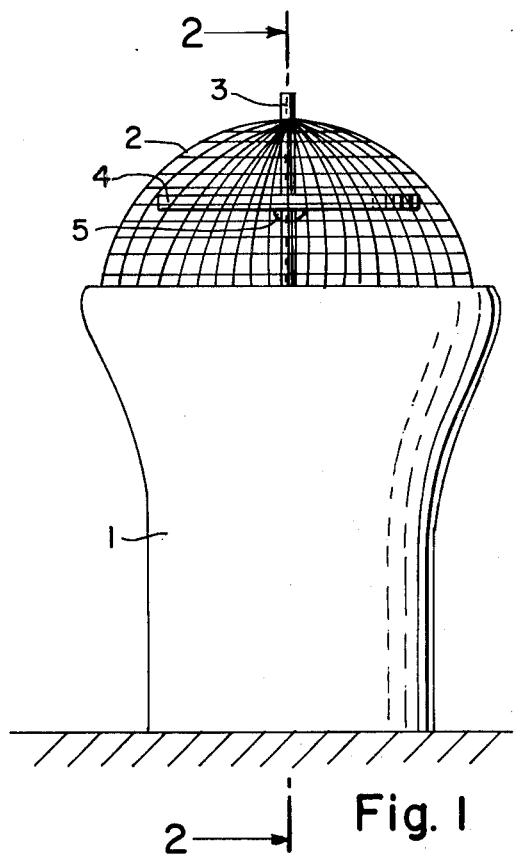

United States Patent [19]

Rogers

[11] 4,198,375
[45] Apr. 15, 1980

[54] INCENSE BURNER

[76] Inventor: Patrick J. Rogers, 2520 NW 42nd Ave., Lauderhill, Fla. 33313

[21] Appl. No.: 893,899

[22] Filed: Apr. 6, 1978

[51] Int. Cl.² .............................................. A61L 9/02
[52] U.S. Cl. .................................... 422/126; 422/125
[58] Field of Search .................. 21/111, 116; 422/125, 422/126

[56] References Cited

U.S. PATENT DOCUMENTS

| 118,126 | 8/1871 | Hastings | 21/116 |
| 1,801,538 | 4/1931 | Briscoe | 21/116 |
| 1,973,958 | 9/1934 | Jones | 21/116 |

FOREIGN PATENT DOCUMENTS 435680 5/1948 Italy ........................................... 21/116

Primary Examiner—Joseph Scovronek
Assistant Examiner—Roger F. Phillips
Attorney, Agent, or Firm—Bernard Ouziel

[57] ABSTRACT

An incense burner consisting of an exterior receptacle fitted with an ash collecting basket supporting a lighter within said receptacle and an axially disposed spindle. A disc having a plurality of circumferentially disposed holes dimensioned to accept sticks of incense is supported on said spindle above said receptacle and a wire mesh cap is fitted over said disc at the top of the receptacle. The disc can be rotated to permit selective ignition of one or more incense sticks.

5 Claims, 4 Drawing Figures

U.S. Patent       Apr. 15, 1980       4,198,375

INCENSE BURNER

This invention relates to an incense burner and, more particularly, to a self-contained incense burner having means for safely holding, igniting and burning a plurality of incense sticks.

Numerous means exist for igniting and burning sticks of incense, each with disadvantages avoided by the present invention. For example, in one arrangement incense is held in one hand where it is ignited before being placed on the top of a solid horizontal surface of a receptacle where it rests until extinguished. This technique presents the risk of burns to the hand holding the stick, especially when it is short. It also frequently results in the incense stick being wastefully extinguished before being fully consumed. Another technique is used with longer sticks of incense which are ignited and then placed upright to stand within surfaces such as a soil filled pot. This technique presents the hazard of the stick falling over with ashes spreading outside of the receptacle in which it rests.

It is a general object of this invention to provide an incense burner that will conveniently and safely ignite and retain for complete combustion one or more sticks of incense in a manner which eliminates the hazards of ignition and ash deposition.

Briefly, in accordance with the features of my invention, I provide an incense burner consisting of an exterior receptacle containing an ash collecting basket that supports a lighter within the receptacle and an axially disposed spindle upon which a disc having a plurality of circumferentially disposed holes dimensioned to accept sticks of incense is rotatably supported above said receptacle. A wire mesh cap may be fitted on said spindle over the top of said receptacle. In this fashion the disc may be rotated so that an incense stick is positioned over the lighter which can be operated for safe ignition of the incense stick. After ignition the incense stick may be rotated away from the lighter to a position over the collecting basket so that ashes resulting from the ignition will fall within the receptacle to the collecting basket where they remain until removed.

Figure 2:
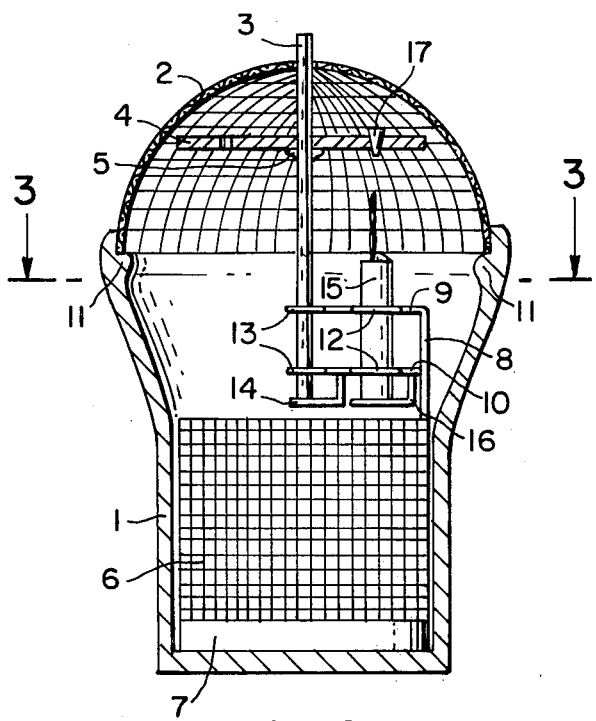
Figure 3:
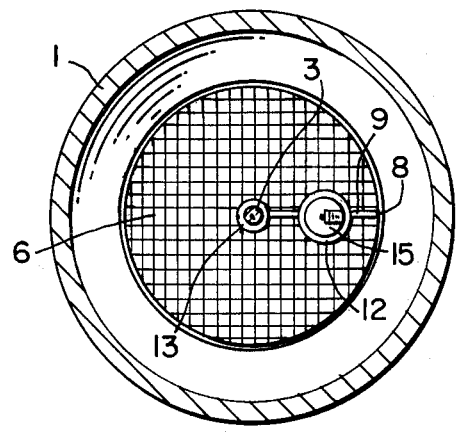

Further features, objects and advantages of my invention will become apparent upon consideration of the following detailed description in conjunction with the drawing in which:

FIG. 1—is a side view of the incense burner assembly;

FIG. 2—is a detailed cross-sectional view taken through 2—2 of FIG. 1;

FIG. 3—is a top cross-sectional view of FIG. 2 taken through 3—3 of FIG. 2; and

Figure 4:
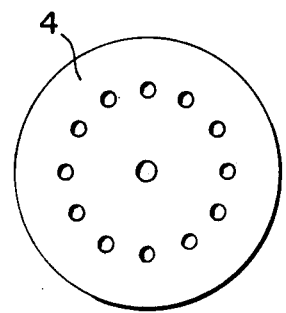

FIG. 4—is a detailed view of the incense supporting disc.

Referring now to the drawing, the incense burner includes an exterior receptacle 1 which may be shaped as shown or in the shape of a decorative vase. Receptacle 1 may be constructed with a shoulder 11 at the inner circumference of its top to support a wire mesh cap 2 as shown. Above the top of receptacle 1 and within cap 2 is an incense supporting disc 4 which may be as shown or constructed from wire mesh and which rests upon shoulder 5 of a spindle 3 in a manner which permits disc 4 to rotate perpendicularly to the axis of receptacle 1.

Fitted within receptacle 1 is an ash collecting basket 6 made preferably from wire mesh and having a solid floor 7 to which ashes drop for collection and removal.

Connected to collecting basket 6 and rising therefrom is a retaining arrangement which may be in the form of a wire rod constructed to have a vertical member 8 from which there extends two horizontal arms 9 and 10. Each arm is constructed to include a larger opening 12 dimensioned to accept a lighter, such as a disposable mechanically operated lighter 15, and a smaller circular opening 13 dimensioned to accept spindle 3. The openings 12 and 13 in arm 9 rest axially above correspondingly dimensioned holes in arm 10. Depending from the bottom of arm 10 are L-shaped restraints 14 & 16, having, at the free ends thereof, a resting surface as will be described further hereinafter.

Spindle 3 is fitted within holes 13 of arms 9 and 10 to rest upon the free end of restraint 14. A cigarette lighter of the disposable type 15 may be inserted within holes 12 of arms 9 and 10 to rest against the free end of restraint 16.

In operation, disc 4 may be loaded with conical sticks of incense 17 placed in one or more of the circumferentially placed holes of disc 4 so that the narrower tip of the incense stick is facing downward towards the top of lighter 15. A stick of incense is ignited by rotating it over the top of cigarette lighter 15 which is then actuated to produce a flame. As will be understood by those versed in the art, lighter 15 will be positioned by appropriate dimensioning of the retainer arrangement so that the flame therefrom can be adjusted to play at the bottom of each overhead incense stick. Once a stick of incense is ignited, disc 4 may be rotated about the axis of spindle 3 so that the ignited stick of incense comes to rest over a clear area of collection basket 6. As the stick of incense burns, ashes will fall through the top of the collecting basket where they will be collected upon floor 7. In this fashion one or more sticks of incense may be ignited simultaneously or sequentially without the danger of burns to the hand and without the danger of ashes falling upon furniture or other places where damage may occur. When an ignited stick of incense is consumed it will likewise fall harmlessly within the collecting basket.

It is understood that the above described arrangement is illustrative of the application of the principles of the invention. Numerous other arrangements may be devised by those skilled in the art without departing from the spirit and scope of the invention. For example, and as will be understood by those versed in the art, numerous other retaining arrangements may be devised including those designed to accommodate different shapes of lighters.

What I claim is:

1. An incense burner comprising an exterior receptacle, an ash collecting basket fitted within and contiguous to the inner walls of said receptacle, a spindle supported axially and partially within said exterior receptacle, an incense retaining plate held upon and in a plane perpendicular to said spindle, said plate having a plurality of apertures dimensioned to retain sticks of incense, a flame producing means, and a retaining structure contiguous to said basket shaped to accept and hold said flame producing means below said plate and to accept and hold said spindle in place while permitting rotation of said plate about an axis through said spindle.

2. An incense burner in accordance with claim 1 wherein said incense retaining plate is a circular disc and said apertures thereof are circumferentially placed upon a diameter smaller than the diameter of said collecting basket.

3. An incense burner in accordance with claim 2 wherein said flame producing means is a desposable mechanically operated lighter.

4. An incense burner in accordance with claim 3 wherein the distance between the top of said flame producing means and said retaining plate is in the range of one to six inches.

5. An incense burner in accordance with claim 4 further comprising a wire mesh dome fitted over the top of said receptacle to enclose said incense retaining plate.

* * * * *